United States Patent [19]

Hommeltoft et al.

[11] Patent Number: 5,245,100

[45] Date of Patent: * Sep. 14, 1993

[54] ALKYLATION PROCESS

[75] Inventors: Sven I. Hommeltoft, Hillerod; Haldor F. A. Topsoe, Vedbeek, both of Denmark

[73] Assignee: Haldor Topsoe, S.A., Denmark

[ * ] Notice: The portion of the term of this patent subsequent to Jun. 15, 2010 has been disclaimed.

[21] Appl. No.: 876,017

[22] Filed: Apr. 28, 1992

Related U.S. Application Data

[63] Continuation-in-part of Ser. No. 626,956, Dec. 13, 1990.

[30] Foreign Application Priority Data

Dec. 18, 1989 [DK] Denmark .............................. 6439/89
Jun. 8, 1990 [DK] Denmark .............................. 1402/90

[51] Int. Cl.$^5$ ............................ C07C 2/56; C07C 2/58
[52] U.S. Cl. ..................................... 585/720; 585/721; 585/730
[58] Field of Search ........................ 585/720, 721, 730

[56] References Cited

U.S. PATENT DOCUMENTS 3,778,489 12/1973 Parker et al. ........................ 585/730
3,976,759 8/1976 Bennett et al. ........................ 502/20

Primary Examiner—Anthony McFarlane
Assistant Examiner—Nhat D. Phan
Attorney, Agent, or Firm—Ostrolenk, Faber, Gerb & Soffen

[57] ABSTRACT

Aliphatic hydrocarbons are alkylated in the presence of a fluorinated sulphonic acid catalyst. The catalyst, which is adsorbed on a polar contact material, is pushed sequentially through first and second reactors by a feedstream and is then recycled back to the first reactor without reversing the flow direction of the process stream.

5 Claims, 1 Drawing Sheet

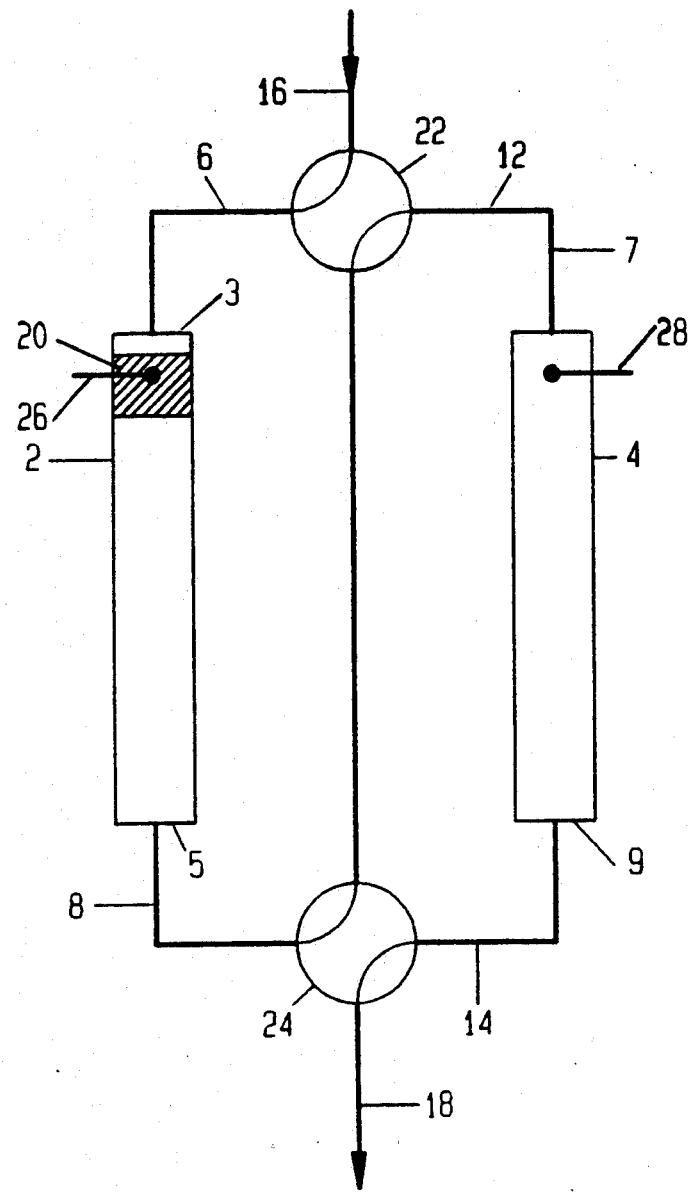

ALKYLATION PROCESS

This application is a continuation in part of prior application Ser. No. 626,956 filed on Dec. 13, 1990, (recently allowed) which by reference is specifically incorporated herein.

BACKGROUND OF THE INVENTION

1. Field of the Invention

The present invention relates to improvements in the supported liquid phase alkylation of aliphatic hydrocarbons in the presence of a fluorinated sulphonic acid catalyst.

2. Description of the Related Art

Acid catalyzed alkylation of aliphatic hydrocarbons with olefinic hydrocarbons is a well known process for the preparation of high octane gasoline products. In the past, alkylation of hydrocarbons has been accomplished in liquid phase by mixing paraffins and olefins in the presence of a strong acid catalyst and stirring the mixture until the alkylation reaction was completed.

To date the only employed acid catalysts in the industrial alkylation of aliphatic hydrocarbons are concentrated sulphuric acid or anhydrous hydrofluoric acid, the strength of which may be increased by addition of a Lewis acid, such as $BF_3$ or $SbF_5$.

The known acid catalyzed batch processes require large reaction volumes and thorough mixing of the alkylation mixture by mechanical mixing means in order to provide intimate contact between the acid catalyst, the reacting hydrocarbons and the olefinic alkylating agent.

Although being very efficient catalysts a major drawback of the known acid catalysts are their environmental and health risk, when used in large amounts such as in the batch processes.

Beside of being hazardous materials sulphuric acid and hydrofluoric acid are rather unstable or aggressive compounds under the reaction conditions used in the known alkylation processes. At ambient conditions hydrofluoric acid is a volatile gas, which necessitates the alkylation process to be carried out at low temperatures or at elevated pressure. While sulphuric acid is a liquid with a high boiling point and much easier to contain in the event of an accident, it is consumed in considerable amounts during the process by reduction to volatile sulphur dioxide and other unwanted products.

Utilization of fluorinated sulphonic acids, as efficient catalysts during the alkylation of aliphatic hydrocarbons with olefins, is disclosed by the prior application Ser. No. 626,956. Besides being less volatile compounds with appreciatively minor environmental and health risk than hydrofluoric acid, the fluorinated sulphonic acids, when used as alkylation catalysts, are not disintegrated during the alkylation reaction as is the case for sulphuric acid. In essence, the prior application is related to supported liquid phase alkylation of a process stream including a hydrocarbon substrate and an olefinic alkylating agent, by contact with a fluorinated sulphonic acid catalyst in a fixed bed alkylation reactor of polar contact material, in which there is established on the contact material a reaction zone with the fluorinated sulphonic acid catalyst adsorbed within a confined area of the contact material. In the reaction zone the process stream is converted at alkylating conditions to a product stream of alkylated hydrocarbons by catalysis of the fluorinated sulphonic acid adsorbed on the contact material.

During the alkylation reaction, the acid catalyst and, consequently, the reaction zone, move to a new position located nearer the outlet end of the alkylation reactor by interaction with the process stream flowing through and reacting in the zone.

As a theoretical explanation, the elution of the catalyst acid is caused by reactions of the fluorinated sulphonic acid with olefins in the process stream to an ester, which is less polar than the original acid and more loosely adsorbed on the contact material in the reaction zone. The ester moves together with the process stream until it is cleaved to yield the free acid and a carbonium-ion, which reacts with the hydrocarbon substrate to form alkylated hydrocarbons.

The migration speed of the acid catalyst in the reactor and on the contact material is thereby much lower than the migration speed of the hydrocarbons in the process and product stream resulting in a much longer elution time for the acid catalyst than the elution time for the hydrocarbons.

During the migration of the acid catalyst on the contact material, the catalytic activity of the fluorinated sulphonic acid is substantially retained and the acid is still catalytic active, when the reaction zone reaches the reactor outlet.

It is thus possible to reuse the acid catalyst without recovery of the acid, as it reaches the outlet end of the alkylation reactor by reversing the flow direction of the process stream introduced into the alkylation reactor. The reaction zone is then pushed towards the opposite end of the reactor by interaction with the process stream as described above.

Thus, in order to reuse the acid catalyst by the process of the previous application, the acid has to be pushed inside the reactor forth and back on the contact material by periodically reversing the flow direction of the process stream introduced into the reactor.

Despite of its high alkylation efficiency a general drawback of the above process lies in the alternating forth and back flow of the process stream through the contact material. Thereby, a slight fluidization of the contact material may be introduced by the process stream resulting eventually in distortion of the reaction zone by unsymmetric distribution of the acid catalyst in the fluidized contact material. This may further lead to by-pass regions in the reaction zone and thus to diminished alkylation efficiency.

SUMMARY OF THE INVENTION

It has now been found that distortion of the reaction zone during acid catalyzed supported liquid phase alkylation process can be avoided, when carrying out the process in at least two reactors connected in series and passing a process stream for hydrocarbon substrate and alkylating agent sequentially in one direction through the reactors being alternatingly provided with a reaction zone of a fluorinated sulphonic acid catalyst adsorbed within a confined area of a polar contact material arranged in the reactors. The improved process involves the concept of pushing the acid catalyst adsorbed on the contact material by interaction with the process stream sequentially through the first and second reactor and recycling the acid back to the first reactor whenever it leaves the second reactor, without reversing the flow direction of the process stream. Because of the acid catalyst is cycled between at least two reactors an attendant advantage of the process is that the contact material in the reactors can be flushed after the acid catalyst has been transferred to the following reactor in the series. Thereby, residual unconverted alkylation reactants in the reactor are brought in contact with the acid catalyst in the reactor containing the acid catalyst.

Accordingly, the present invention provides an improved process for the supported liquid phase alkylation of a hydrocarbon substrate with an olefinic alkylating agent in the presence of a fluorinated sulphonic acid catalyst in at least two reactors connected in series, each reactor containing a fixed bed of particulate polar contact material, which process comprises alternatingly establishing in a first reactor and a second reactor on the polar contact material a reaction zone with the fluorinated sulphonic acid catalyst adsorbed within a confined area of the contact material;

passing a stream of the hydrocarbon substrate and alkylating agent at alkylating conditions in one flow direction sequentially through the first and second reactor and the second and first reactor;

recovering a product stream of alkylated hydrocarbon substrate from the first and second rector; and passing a stream of the hydrocarbon substrate and/or alkylated hydrocarbon substrate sequentially through the first and second reactor and through the second reactor and first reactor in the same flow direction as the process stream when the fluorinated sulphonic acid catalyst has passed from the first to the second reactor or from the second to the first reactor.

Suitable fluorinated sulphonic acids for use as catalyst in the inventive process are fluorinated alkane sulphonic acids, including $C_1$–$C_4$ perfluorinated alkane sulphonic acids.

A preferred fluorinated sulphonic acid is trifluoromethanesulphonic acid.

Due to the high efficiency and stability of the fluorinated sulphonic acid catalyst during the alkylation process, small amounts of the acid applied on the contact material ensure high yields of alkylated products.

Convenient contact materials are any of the polar and non-basic refractory materials. Preferred materials are silica, zirconia, titania, the oxides of tin and the lanthanides or mixtures thereof.

Within the reaction zone the process stream of hydrocarbon substrate comprising paraffins, such as $C_3$–$C_{10}$ isoalkanes, and olefinic alkylating agent typically $C_2$–$C_{10}$ olefins, is converted at alkylating conditions by catalysis of the fluorinated sulphonic acid adsorbed on the contact material to a product stream containing alkylated products.

The process steam may be passed through the alkylation reactor at temperatures of between $-50°$ and $100°$ C., and at a pressure varying in the range of between 1–100 bar abs. depending on the composition of the process stream and the actual reaction temperature.

The weight ratio of the hydrocarbon substrate to the alkylating agent in the process stream may, thereby, vary between 1.5:1 and 30:1.

By interaction with the process stream the acid catalyst is continuously desorbed and readsorbed on the contact material as further explained hereinbefore. Having reached the outlet end of the reactor, the acid catalyst is transferred together with the reacting process stream to the inlet end of the following reactor and adsorbed within a confined area of the contact material in this reactor and processed in similar manner as in the first reactor. After the acid catalyst has reached the outlet end of the second reactor the process stream is in a subsequent alkylation cycle introduced into the second reactor and sequentially passed to the second and first reactor with the same flow direction as in the previous cycle. The acid catalyst is thereby recycled to the inlet of the first reactor.

During the alkylation cycles a stream of alkylated products is withdrawn from that reactor, having the acid catalyst adsorbed on the contact material.

Whenever the acid is cycled from one to the other reactor, the reactors are flushed with hydrocarbon substrate and/or alkylated product in the same flow direction as in the alkylation cycles in order to transfer unreacted alkylation agent to the transferred reaction zone.

Thereby, a stream of the hydrocarbon substrate and/or alkylated product is sequentially passed through the reactors at the same process conditions as the previous process stream.

BRIEF DESCRIPTION OF THE DRAWING

In the following, the invention will further be explained by reference to the drawing, in which the FIGURE represents a simplified process diagram of a specific embodiment of the invention.

DETAILED DESCRIPTION OF THE PREFERRED EMBODIMENT

In the reactor system as schematically shown in the FIGURE a first reactor 2 is connected in series with a second reactor 4 through lines 8, 10, and 12. The system further comprises feed supply lines 16 and 6 and effluent lines 14 and 18. Lines 16 and 14 are connectable to line 12 and 10, respectively, by four-way valves 22 and 24. Reactors 2 and 4 are each provided with a fixed bed of polar contact material, on which a moveable reaction zone 20 is alternatingly provided within reactor 2 and 4. Reaction zone 20 has a fluorinated sulphonic acid catalyst adsorbed on the contact material within the area of the zone.

A first alkylation cycle reaction zone 20 is initially established at inlet end 3 of reactor 2. A process stream of a hydrocarbon substrate, such as $C_3$–$C_{10}$ isoalkanes and an alkylating agent such as $C_2$–$C_{10}$ olefins is then introduced into reactor 2 via line 16 and 6. In reactor 2 the process stream is converted at a temperature of between $-50°$ C. and $100°$ C. and a pressure varying in the range of between 1–100 bar to an alkylate product stream by passage through the reaction zone. The product stream is then further passed to reactor 4 through lines 8, 10, and 12 and withdrawn at outlet end 9 of reactor 4 through lines 14 and 18. As further explained hereinbefore, reaction zone 20 is during the alkylation cycle gradually moved by contact with the process stream towards outlet end 5 of reactor 2 through desorption and readsorption of the acid catalyst on the contact material.

Having reached outlet end 5, the acid catalyst is then transferred together with the reacting process stream to reactor 4, where the reaction zone is establish at inlet end 7 of reactor 4, by adsorption of the acid catalyst within a confined area of the polar contact material contained in reactor 4.

Because of the acid catalyzed alkylation reaction is exothermic the transfer of the acid catalyst from one reactor to the other can be monitored by thermocouples 26, 28 installed at the inlet ends of the reactors. A change in temperature will be monitored at inlet end 7, when the acid catalyst has been transferred from reactor 2 to reactor 4. Introduction of the process stream into reactor 2 is then stopped and the reactor flushed with a hydrocarbon stream being introduced into reactor 2 through lines 16 and 6 and cycled to reactor 4 via line 8, 10, and 12. During flushing of reactor 2 residual alkylating agent left in reactor 2 is passed together with the hydrocarbon stream to the reaction zone now established in reactor 4 and further used in the alkylation of the hydrocarbon stream.

After a predetermined flushing time introduction of the hydrocarbon stream is stopped, and valve 22 is switched to give passage from lines 16 to 12, and from lines 10 to 6 and valve 24 to give passage from lines 14 to 10 and from lines 8 to 18.

In a subsequent alkylation cycle, the process stream is now introduced through line 16 and 12 into reactor 4.

The process stream in reactor 4 is passed through the reaction zone established in the reactor and converted to an alkylated product stream as described hereinbefore. The product stream is then cycled to reactor 2 through lines 14, 10 and 6 and withdrawn from reactor 2 via lines 8 and 18.

Similar to the previous alkylation cycle, the acid catalyst adsorbed on the contact material in reactor 4 moves slowly on the contact material from inlet end 7 to outlet end 9 by interaction with the process stream. Having reached outlet end 9, the acid catalyst is transferred together with the process stream to inlet end 3 of reactor 2. The transfer of the acid catalyst is thereby mentioned as an increase of temperature at inlet end 3 measured through thermocouple 26 arranged in inlet end 3. Immediately after a temperature increase is observed at inlet end 3, introduction of the process stream into reactor 4 is stopped, and the reactor is flushed with a hydrocarbon stream being passed to reactor 4 and cycled to reactor 2 similar to the previous process stream. Thereby, residual alkylating agent in reactor 4 is transferred to reactor 2 and reacted in the reaction zone now established in reactor 2 by adsorption of the transferred acid catalyst on the contact material in reactor 2.

Subsequent alkylation and flushing cycles are then carried out as described above.

EXAMPLE

A hydrocarbon substrate consisting of isobutane was alkylated with a 1-butene alkylating agent in the presence of trifluoromethanesulphonic acid catalyst in a reaction system shown and described hereinbefore by reference to the drawings.

The reactor system consisted of two stainless steel tubes (316 SST) each with a length of 6 m and an inner diameter of 0.25 inches. The reactors were loaded with a contact material of Silica gel (Silica Gel 100, supplied by E. Merck, FRG; particle size 0.2-0.5 mm).

The reactors were connected in series with recirculation as shown in the FIGURE.

During the alkylation cycles a process stream of isobutane and 2-butene (weight ratio of 9:1) was passed sequentially through the reactors at a flowrate of 5 g/min. and a temperature of ÷10° C. and a pressure of 10 bar.

Before the first alkylation cycle 10 ml of trifluoromethanesulphonic acid catalyst were applied on the contact material at the inlet of the first reactor. When the acid catalyst has reacted the inlet of the second reactor, the flow of process stream was stopped and the reactors flushed with 120 g isobutane introduced into the first reactor with a flow rate of 5 g/min.

In the subsequent alkylation cycle, the process stream was passed at the same conditions as in the first alkylation cycle sequentially through the second and first reactor, whereby the acid catalyst was transferred back to the first reactor.

In a first experiment 9 alkylation cycles with intermediate flushing cycles and during a second experiment 14 alkylation cycles and flushing cycles were carried out as described above.

The results obtained by the experiments are summarized below in the Table.

TABLE

Trifluorosulphonic acid catalysed alkylation

| Experiment No. | Alkylate yield wt % of 1-butene | Alkylate Product* Composition (wt %) | | | |
|---|---|---|---|---|---|
| | | $C_{5-7}$ | $C_8$ | $C_{9+}$ | RON |
| 1 | 198 | 11 | 75 | 14 | 98 |
| 2 | 196 | 10 | 76 | 14 | 98 |

*After debutanization.

We claim:

1. A process for liquid phase alkylation of a hydrocarbon substrate with an olefinic alkylating agent in the presence of a fluorinated sulphonic acid catalyst in at least a first reactor and a second reactor connected in series, each reactor containing a fixed bed of particulate polar contact material, the process comprising the steps of:
   a) establishing a reaction zone on the polar contact material located in the first reactor, the fluorinated sulphonic acid catalyst being adsorbed on a confined area of the contact material in the first reactor;
   b) passing a stream of the hydrocarbon substrate and alkylating agent at a alkylating conditions in a first flow direction sequentially through the first and second reactors;
   c) recovering a product stream of alkylated hydrocarbon substrate from the second reactor; and
   d) interrupting step b) and passing a stream of hydrocarbon substrate and alkylating agent at alkylating conditions sequentially through the second reactor and the first reactor.

2. The process of claim 1, wherein the fluorinated sulphonic acid catalyst comprises trifluoromethanesulphonic acid.

3. The process of claim 1, wherein the particulate polar contact material is selected from the group consisting of silica, zirconia, titania, oxides of tin, oxides of lanthanides, and mixtures thereof.

4. The process of claim 1, wherein steps b) and d) include passing fluorinated sulphonic acid catalyst sequentially through the first and second reactors and sequentially through the second and first reactors, respectively.

5. The process of claim 1, further comprising the step of alternating the flow of the hydrocarbon substrate and alkylating agent between: 1) sequentially through the first and the second reactors; and 2) sequentially through the second and the first reactors.

* * * * *